(12) United States Patent
Carrozzi et al.

(10) Patent No.: US 6,377,830 B1
(45) Date of Patent: Apr. 23, 2002

(54) PATIENT TABLE IN COMBINATION WITH BIOMEDICAL APPARATI LIKE MAGNETIC RESONANCE IMAGING MACHINE

(75) Inventors: Alessandro Carrozzi, La Spezia; Fabio Rezzonico, Como; Orfeo Contrada; Gianni Sarasso, both of Genoa; Alessio Fachinato, Sant'Olcese, all of (IT)

(73) Assignee: Esaote, S.p.A., Casale Monferrato (IT)

( * ) Notice: Subject to any disclaimer, the term of this patent is extended or adjusted under 35 U.S.C. 154(b) by 0 days.

(21) Appl. No.: 09/412,752

(22) Filed: Oct. 5, 1999

(30) Foreign Application Priority Data

Oct. 5, 1998 (IT) .......................................... SV98A0052

(51) Int. Cl.[7] .................................................. A61B 5/00
(52) U.S. Cl. ...................... 600/407; 600/415; 600/425; 5/601; 378/209
(58) Field of Search ................................ 600/407, 415, 600/425; 378/195, 198, 208, 209; 5/601

(56) References Cited

U.S. PATENT DOCUMENTS

| 2,845,543 | A |   | 7/1958  | Hansen et al. |
| 3,466,439 | A |   | 9/1969  | Setälä |
| 4,062,518 | A |   | 12/1977 | Stivender et al. |
| 5,329,924 | A |   | 7/1994  | Bonutti |
| 5,541,515 | A |   | 7/1996  | Tsujita |
| 5,997,176 | A | * | 12/1999 | Fairleigh ................... 378/196 |
| 6,011,396 | A | * | 1/2000  | Eckels et al. ............... 324/319 |
| 6,152,598 | A | * | 11/2000 | Tomisaki et al. ........... 378/209 |
| 6,195,578 | B1 | * | 2/2001 | Distler et al. ............... 600/415 |

FOREIGN PATENT DOCUMENTS

| DE | 352306      | 4/1922 |
| EP | 0 825 450 A2 | 2/1998 |

* cited by examiner

*Primary Examiner*—Ruth S. Smith
(74) *Attorney, Agent, or Firm*—Burns, Doane, Swecker & Mathis, L.L.P.

(57) ABSTRACT

A patient table is used in combination with a biomedical apparatus such as a magnetic resonance imaging machine. The table includes a supporting surface sized to accommodate at least a part of the patient's body. At least one recess is formed in one or more areas of the supporting surface, these recesses being open at the peripheral edge of the supporting surface. The table is formed of first and second parts that can be angled relative to one another. The table can be swung horizontally to relative positions relative to the machine and locked in selected ones of the positions.

30 Claims, 10 Drawing Sheets

PATIENT TABLE IN COMBINATION WITH BIOMEDICAL APPARATI LIKE MAGNETIC RESONANCE IMAGING MACHINE

BACKGROUND OF THE INVENTION

1. Field of the Invention

The invention relates to a patient table, or similar, particularly in combination with biomedical apparati like magnetic resonance imaging machine comprising a supporting surface which has such a size as to be able to accommodate at least a part of the patient body.

2. Description of Related Art

At present, patient tables, especially those for bearing the patient during diagnostic and therapeutic treatment, by using machines for diagnosis and therapy, are deemed to be separate from the structure of these machines. In order to allow limbs or anatomic regions of the patient body to be inserted into the operating area of the machine, such as an operating surface, a chamber or a cavity two solutions are essentially applied.

When machines allow to do so, the table, having a substantially conventional shape is fully or partially inserted into the structure thereof. This solution involves a huge size of machines, which have a very high purchase and installation cost. Large machines are generally cumbersome and heavy and cannot be placed in premises having a normal construction as regards volume and resistance of floors. This involves cost increases, which are added to the higher cost of the machine.

In Nuclear Magnetic Resonance Imaging machines, the weight problem is important, and the dimensional problem also affects installation costs when, for instance, machines must be enclosed by shielding cages which, by their huge volume, usually have no light construction.

An alternative solution, generally used with low and medium size and low and medium cost machines, particularly in Nuclear Magnetic Resonance, consists in simply placing tables next to the operating surfaces, chambers or cavities of machines. This can be also done by providing coupling constraints between the two structures, in order to obtain certain relative positions, although the machines and the table are always separate and distinct units, as regards both construction and structural synergy. The overall dimensions of the machine with the addition of the table increases considerably and, substantially, to an extent corresponding to the dimensions of the table. When, e.g. in Nuclear Magnetic Resonance machines, a limb or anatomic region of the patient is to be positioned inside a cavity or onto an operating surface, the patient has to be moved, or convertible arm-chairs must be provided, which have tilting parts or the like, or the dimensions of the supporting surfaces of tables have to be limited to a part of the patient body, i.e. to the part which is intended to stay outside the cavities, chambers or operating surfaces.

Anyway, the above solutions do not involve a synergic relationship between the table and the machine, or the chambers, cavities or operating or work or intervention surfaces thereof.

Further problems also arise when the patient is to be disposed in different orientations within a predetermined range. Here, conventional tables, particularly when combined with low or medium cost machines, involve a considerably larger potential overall size of the table-machine combination.

The invention has the object to provide a patient table which, by using comparatively simple and inexpensive means can be more comfortable and user-friendly, particularly with diagnosis and/or therapy machines.

SUMMARY OF THE INVENTION

The invention achieves the above purposes by providing a table as described herein, comprising at least one recess, in one or more areas of the patient supporting surface, these recesses being open at one or more peripheral edges of this supporting surface.

According to a further characteristic, each recess is associated to a removable insert for complementing the supporting surface. These parts may be coupled in different manners and by using different means.

One embodiment provides that said recesses have a much smaller size than the overall supporting surface of the table and that they form open spaces in said supporting plane, such that they can be covered by the patient body without affecting the support thereof.

In a preferred embodiment, a table has, for instance, a plurality of these recesses, which can be provided in the area of the upper limbs and shoulder, in the area of the neck and head, and in the area of the lower limbs, such as the knee, the foot or similar, i.e. in the end areas of the table.

According to the size of recesses, there may be also provided more of them, for instance in the trunk area.

The means for coupling the complementary inserts are preferably of the sliding type and are provided partly on said inserts, and partly at the delimiting edges of recesses.

Said means may be also provided on the general operating surface of a machine for diagnostic testing and for therapeutic applications.

According to a further characteristic, in order to provide adaptability to several different sizes of operating or work surfaces, inserts may be modular and modules may also have different shapes, so as to allow them to fit the different possible shapes of the operating surfaces.

A further characteristic of the invention advantageously provides a table which is transversely divided into two parts, preferably but not necessarily substantially in the median area, which parts complement each other in jointed coupling.

A preferred construction provides that a part of the table is provided, at its periphery, with a preferably circular guide, completely surrounding it, and extending from one end to the other of the end side of said part of the table, said end side being opposite to the end connected to the other part of the table.

A particularly advantageous configuration of this table provides that a part of the table has a recess whose median axis is oriented coaxially to the central longitudinal axis of the table, which recess has its open side at the end side of the part of the table wherein it is provided, which is opposite to the side connected to the other part of the table.

Here, the part of the table with the recess at its end side substantially consists of a U-shaped frame, whereas the guide for jointing it to the other part of the table is attached all around said U-shaped frame.

The U-shaped frame may also have a circular outside perimeter, coaxial to the arched jointing guide.

Particularly, in order that a certain relative orientation can be maintained between the two parts of the table, there are provided removable means for locking the two parts of the table in the different angular mutual orientation positions.

The two parts of the table may have two legs each, disposed so that the table can be self-supporting, whereas each part cannot be self-supporting in the work position, without the other.

Alternatively, each part may have such a number of legs as to enable a self-support thereof, when separated from the other part. All legs may be wheeled.

Legs may be arranged in such a manner and number that the table may be used as a conventional transport table.

Thanks to the above characteristics, the table in accordance with the invention may be integrated in or complemented by any work or operating surface or any side or wall for delimiting operating chambers or cavities of diagnosis or therapy machines.

The mutual penetration of the work or operating surface and the table allows a considerable reduction of the overall size. Modular solutions of removable complementary inserts allow a table to fit several different operating or work surfaces. The latter are not only work surfaces or operating zones of the machines, but may be also surfaces equipped for performing manual interventions. Hence, one table can fit several different operating conditions, so that the patient need not be frequently transferred for the different interventions.

The embodiment providing a table divided into two separate parts, which may be oriented in any angular position on the horizontal plane allows to simply orient the patient with respect to the operating or work surface, to the operating chamber or cavity, which complement the recess of one of the two parts of the table.

The recessed part of the table advantageously has sliding means for coupling to the side of the machine which is designed to complement the recess/es, for instance by means of sliding guides, preferably along a rectilinear sliding path, directed towards the open side of the recess.

Shock-absorbing or yielding end-of-stroke means are also provided.

The table advantageously consists of a part having the form of a frame whose inner edge has a U-shaped profile, opening on the end side towards the side of the machine which delimits or defines the chamber or the cavity or the surface for bearing the patient, or parts of his/her body inside the machine, whereas a second part of the table is coupled to the first part, so as to allow free orientation on the horizontal plane.

This arrangement is particularly advantageous with machines having access apertures for the patient body on at least three sides of their perimeter.

Particularly, the table provides considerable advantages, when used in combination with Nuclear Magnetic Resonance Imaging machines. In such machines, this configuration equals that of a machine having a C-shaped magnet, i.e. whose cavity may be accessed from three sides of its perimeter. Here, the lower horizontal side of the cavity is the side or surface which is to complement the U-shaped recess of the table.

With such a construction of the magnet, the two parts of the table can have an angular range for mutual orientation of about 180°.

However, if the magnet is composed of two horizontal plates, separated by two or three columns, the angular positions for mutual orientation can extend over 360°, excepting the positions in which the outer part is in line with the columns or uprights. Advantageously, in order to allow the table to be simply coupled to the magnet, i.e. to the side which delimits the cavity, the arched guide for the second part of the table has an angular extension of less than 360°, since it is interrupted at the end aperture of the recess. The orientation angular width between the two parts of the table can be determined in this case by coupling the table on the diametrically opposite part of the magnet structure.

BRIEF DESCRIPTION OF THE DRAWINGS

The characteristics of the invention and the advantages derived therefrom will appear more clearly from the following description of certain exemplary embodiments, illustrated without limitation by the accompanying drawings, in which.

DETAILED DESCRIPTION OF PREFERRED EMBODIMENTS OF THE INVENTION

The embodiments illustrated herein particularly relate to a combination of a table according to the invention and a Nuclear Magnetic Resonance Imaging machine. This combination shall not be deemed to be limited to the scope of the invention. In fact, instead of the lower horizontal side 201 of the magnet cavity, which side 201 complements the recess 301a of the table, the part for complementing the recess 302 of the table may consist of work or operating surfaces, or sides for delimiting operating chambers of any type and/or of any machine for diagnosis and/or therapy.

Since in Nuclear Magnetic Resonance machines, the problems to reduce costs and dimensions are very important, and still directly connected to each other, the combination illustrated and described herein consists of a table and of a Nuclear Magnetic Resonance Imaging machine, and particularly includes a low or medium cost and a low or medium sized machine.

Referring to FIGS. 1 to 9, a Nuclear Magnetic Resonance Imaging machine 1a comprises a magnet part 1. The magnet shown in these figures is U-shaped and defines a cavity with three open sides of its perimeter, while being delimited by an upper side 101, a lower side 201 and a vertical side 301. These three sides form a cover of the magnetic structure and of other operating members, which cover is made of an appropriate material, e.g. of plastic or the like, and has a recess 401, in a predetermined area, for accommodating the fastening base of a receiving coil.

The free end edges of the upper and lower sides 101 and 201 are rounded, preferably with a semicircular profile.

A table 2 is associated to the magnet 1. The table consists of two parts 102, 202. The part 102 has a supporting surface having a hollow or recess 302 having a shape complementary and a size corresponding to the lower side 201 of the magnet 1, while it can have any outer shape, preferably a circular segment shape with an angular extension of more than 180°, such as to fully surround the central U-shaped hollow. The part 102 of the table is designed to be fitted around the side 201 of the magnet 1, which complements the supporting surface. The part 102 of the table is supported by at least a first pair of wheeled legs 3, 4 (see FIG. 4) which are provided at least in the end side for connection to the other part 202 of the table, also supported by a second pair of wheeled legs 3, 4 being provided on the end side opposite to the one connecting to the part 102. The supporting surface of the two parts of the table is at the same level as the side 201 of the magnet 1. The part 202 of the table, named outer part in the disclosure and claims, rests, at the end connecting to the part 102, on a guide 5 which is supported so as to project downwardly, towards the connecting end of the part 202 of the table, by vertical pins 6 and by radial pins 7, arranged radially inside the guide 5. The guide 5 advantageously consists of a cylindrical section which is arched according to the outer cylindrical profile of the part 102 of the table. The part 102 of the table has a covering case 402, for covering the first pair of supporting legs and other members, which, in the magnet-coupling condition, superposes the case 501 of the magnet, providing the machine with a particularly pleasant continuous aspect.

Thanks to this construction, the table 2 may be coupled to the magnet 1, thus forming a complete supporting surface for the patient, having such a size as to be able to comfortably bear the patient body, while reducing the overall dimensions, i.e. the part of the table projecting out of the magnet. Further, the so-called outer part 202 of the table can rotate about the part 102, which is coupled to and complemented by the lower side 201 of the magnet 1, in such a manner that it can have any orientation on the horizontal plane with respect to the part 102. Here, the U-shaped structure of the magnet provides an angular orientation range of about 180°, hence allowing to dispose the patient along an axis parallel to the vertical side 301, along an axis perpendicular thereto, or along axes with intermediate directions on both sides of the axis perpendicular to the vertical side 301.

In combination with machines having magnets with different conformations, the rotation of the part 202 with respect to the part 102 can be either reduced, for instance by using magnets with two open sides perpendicular to each other, or extended, for instance by using magnets in which the cavity is only defined by two sides, e.g. the upper horizontal side and the lower horizontal side, whereas the poles associated to said two sides are spaced by uprights or columns, whose number and size can vary from at least 1 to 2, 3 or more.

In order to use this table, for example to transport the patient, the part 102 may have a pair of wheeled legs also at the ends of the branches of the U-shape. Also, a removable member may be provided for closing the hollow, thereby completing the supporting surface, for example by sliding engagement means.

With particular reference to FIGS. 4, 5, 8, 9 and 10, the part 102 of the table can be slidably coupled to the magnet 1. This may be done by using guide means, one part thereof being associated to the sides of the magnet 1, superposed beneath the branches of the supporting surface with the U-shaped hollow.

Figure 1:
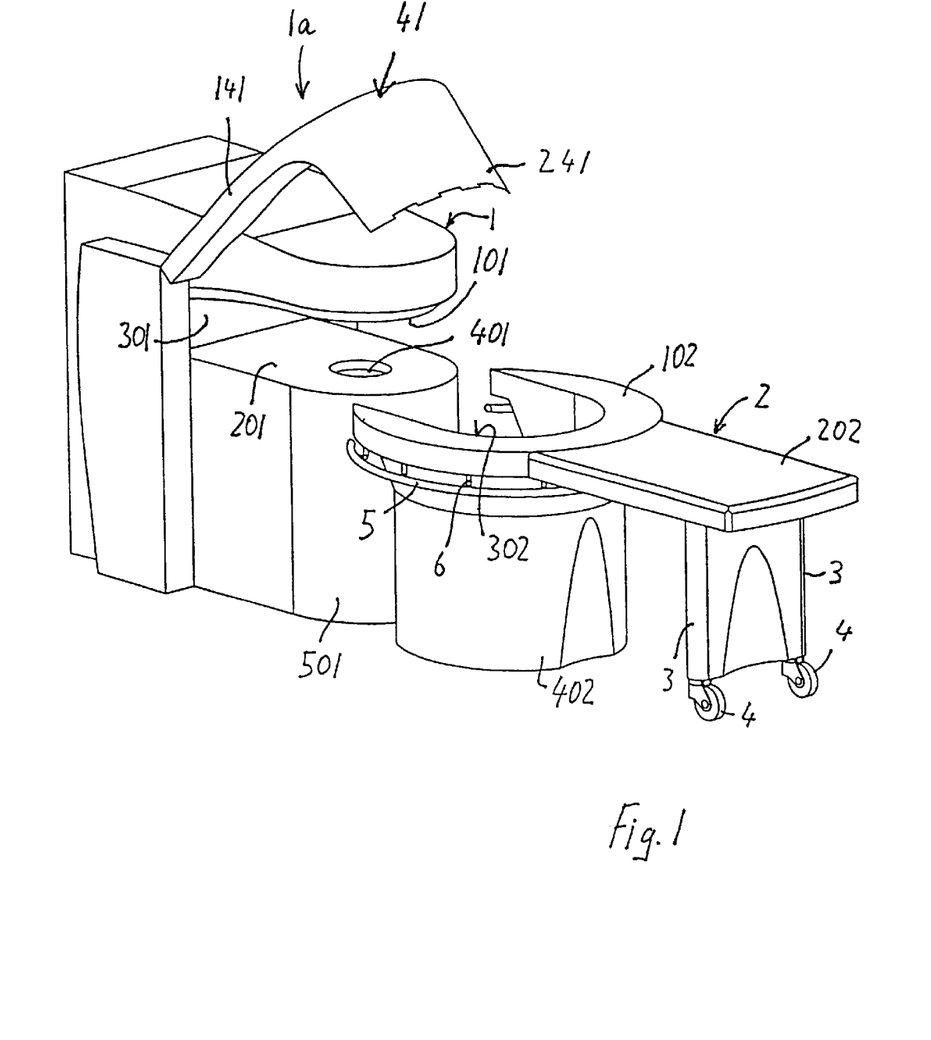
FIG. 1 is a perspective view of a first embodiment of the invention, in which the machine comprises a C-shaped magnet with horizontal poles and a table consisting of two parts, which are jointed or may be oriented on the horizontal plane, the table being uncoupled from the magnet.
Figure 2:
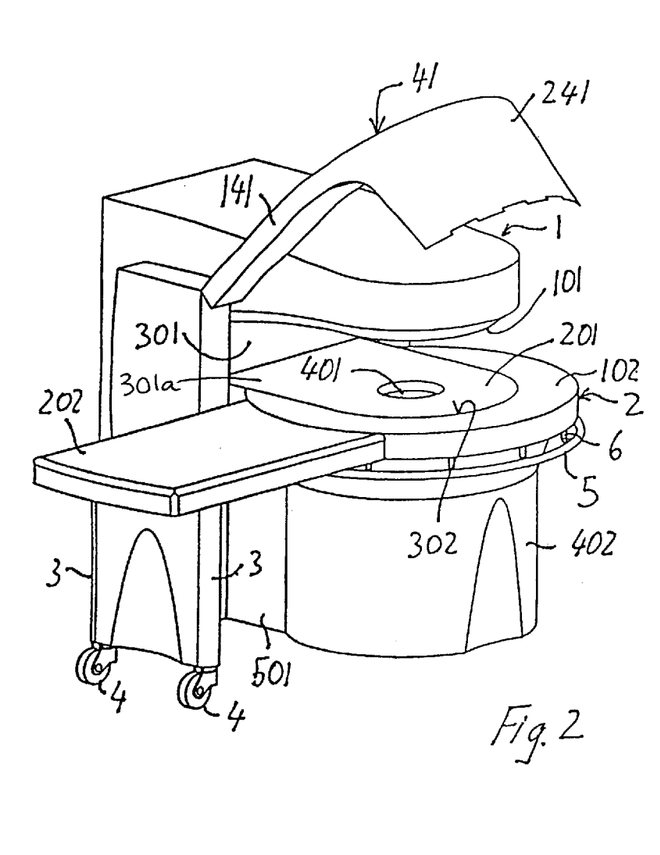
FIG. 2 is a perspective view like that of FIG. 1, in which the table is coupled to the magnet and the part of the table outside the magnet is angularly displaced, with its longitudinal axis being oriented perpendicular to the longitudinal axis of the part of the table coupled to the magnet and with a rigid shielding member in the lifted position.
Figure 3:
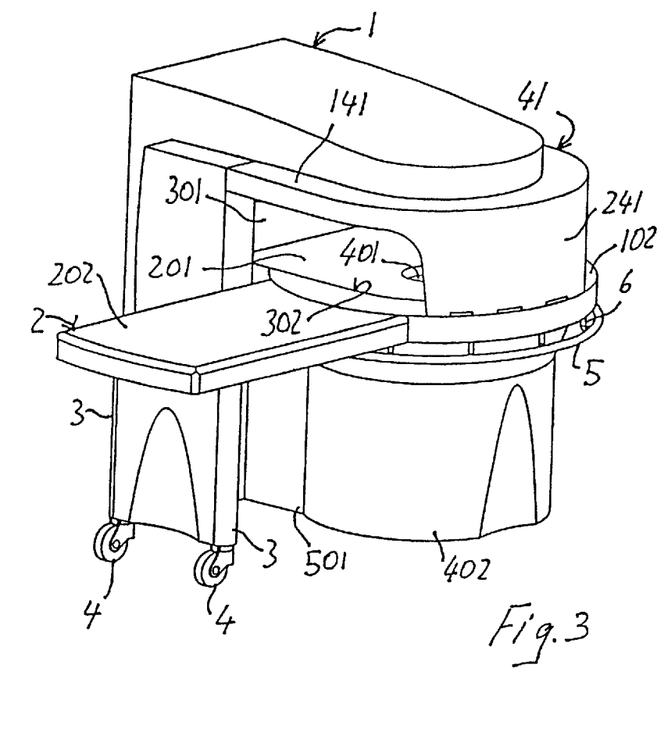
FIG. 3 is a view like that of FIG. 2, in which the shielding member is lowered to the position in which it closes the open front side.
Figure 4:
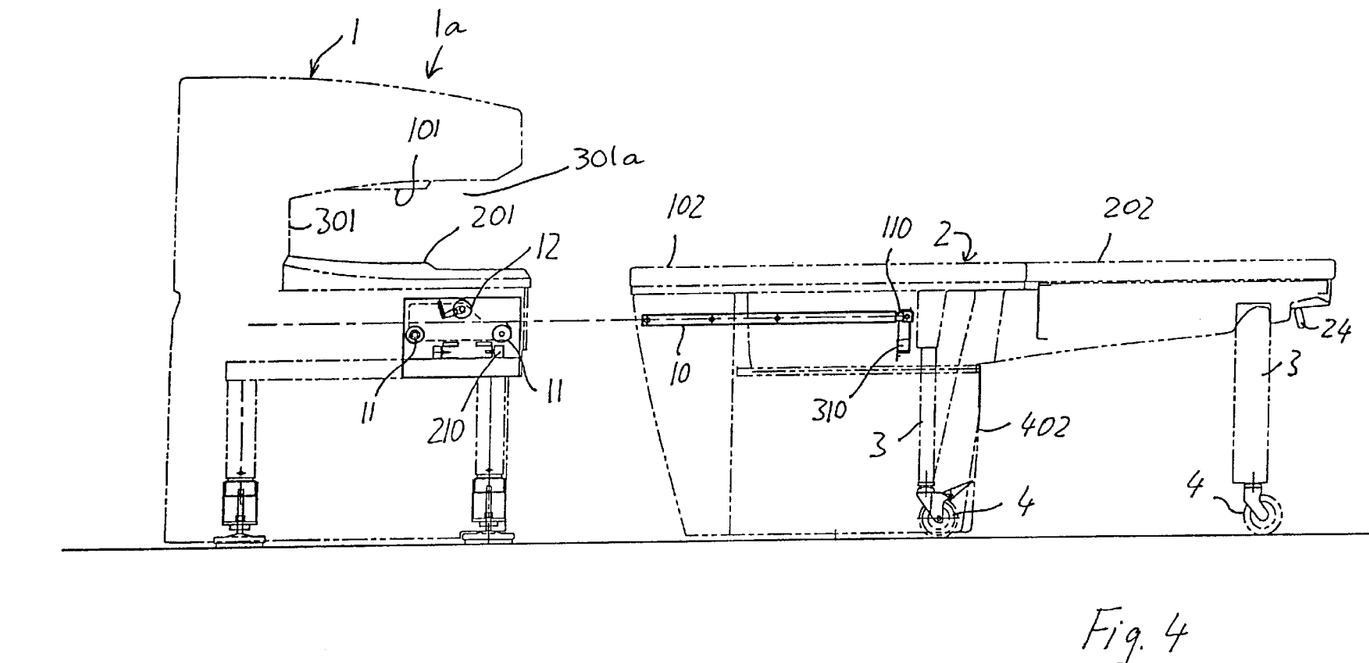
FIGS. 4 and 5 are lateral elevational, partially sectional views of the machine as shown in the previous figures, with the table being uncoupled from and coupled to the magnet respectively.
Figure 5:
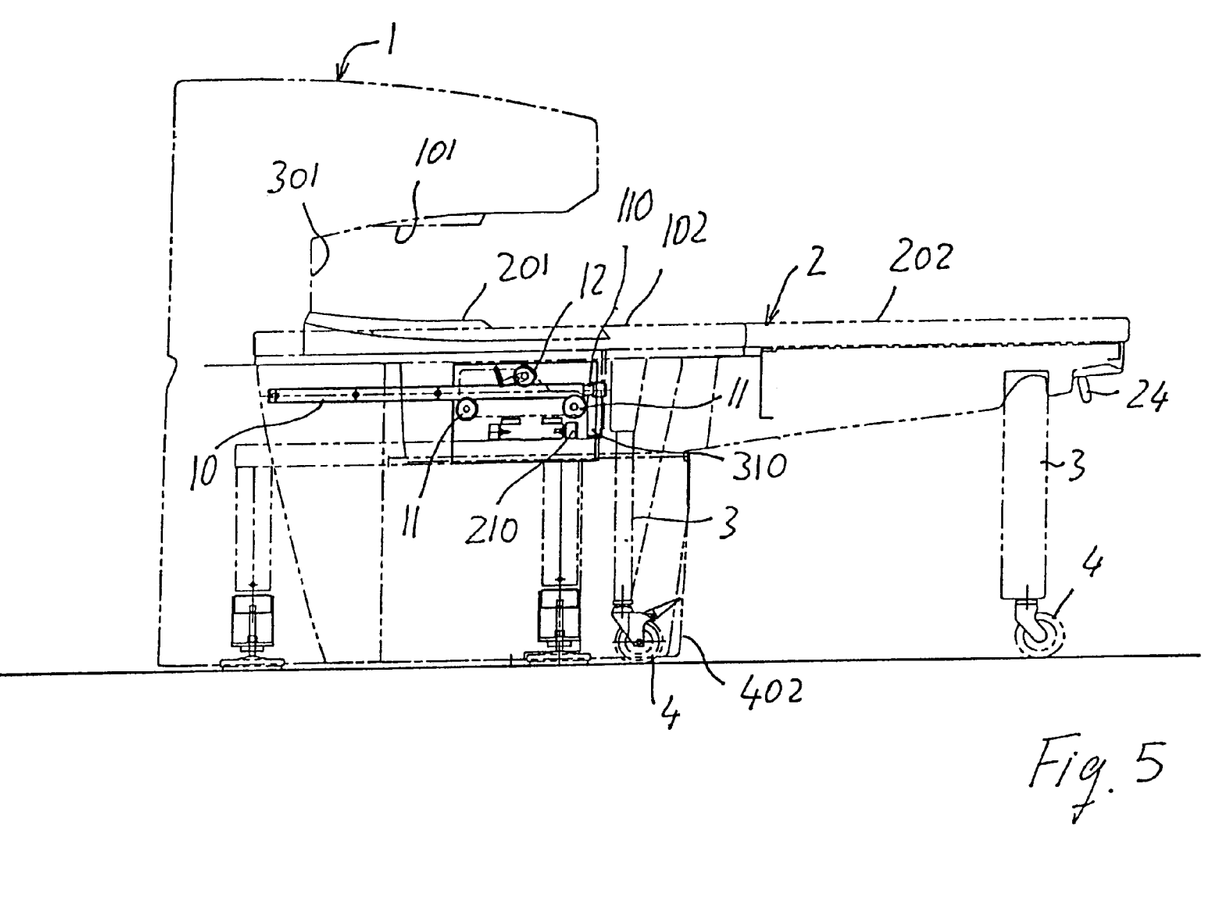
Figure 6:
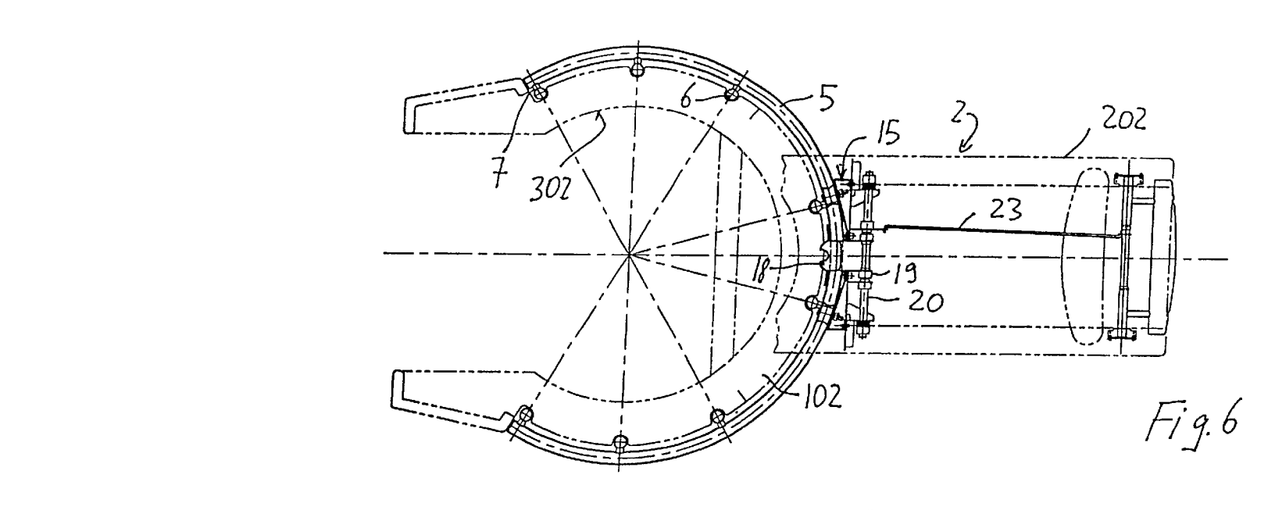
FIGS. 6 and 7 are a top plan view and a lateral view respectively, both partially sectional, of the table as shown in the previous figures.
Figure 7:
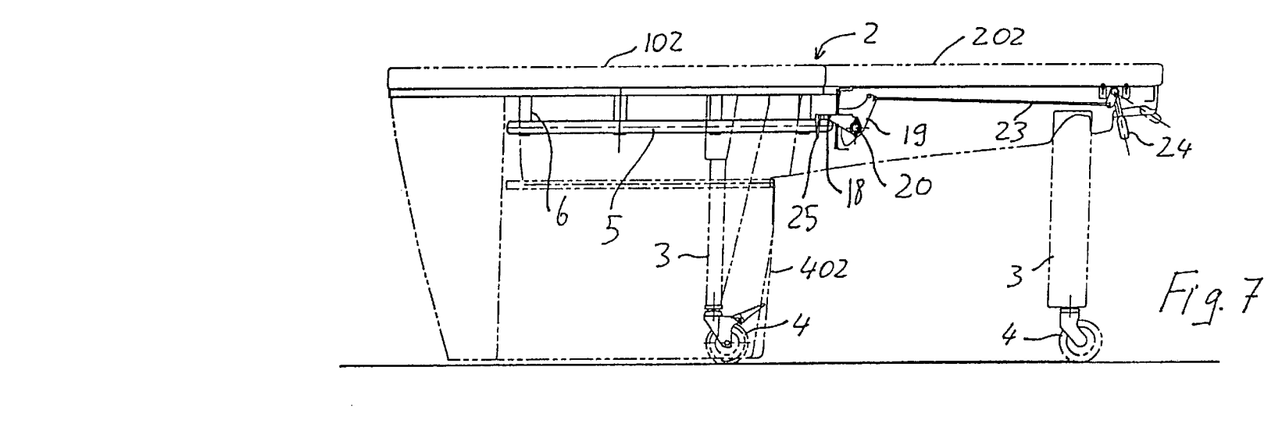
Figure 8:
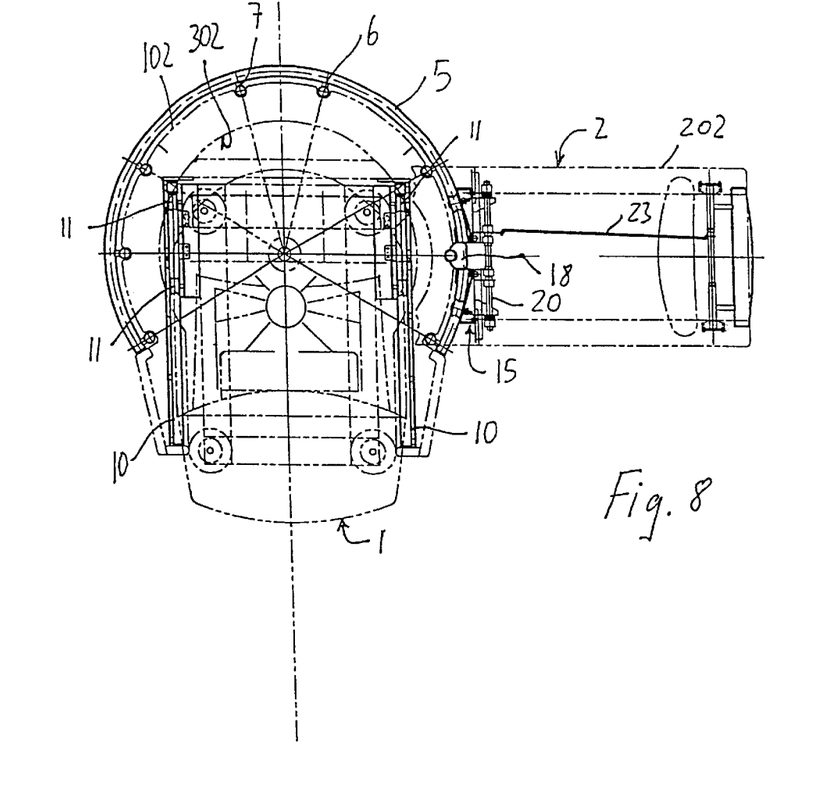
FIGS. 8 and 9 are top plan views of the machine as shown in the previous figures, with the table having the outer part perpendicular to the part coupled to the magnet and being coupled to and uncoupled from the magnet respectively.
Figure 9:
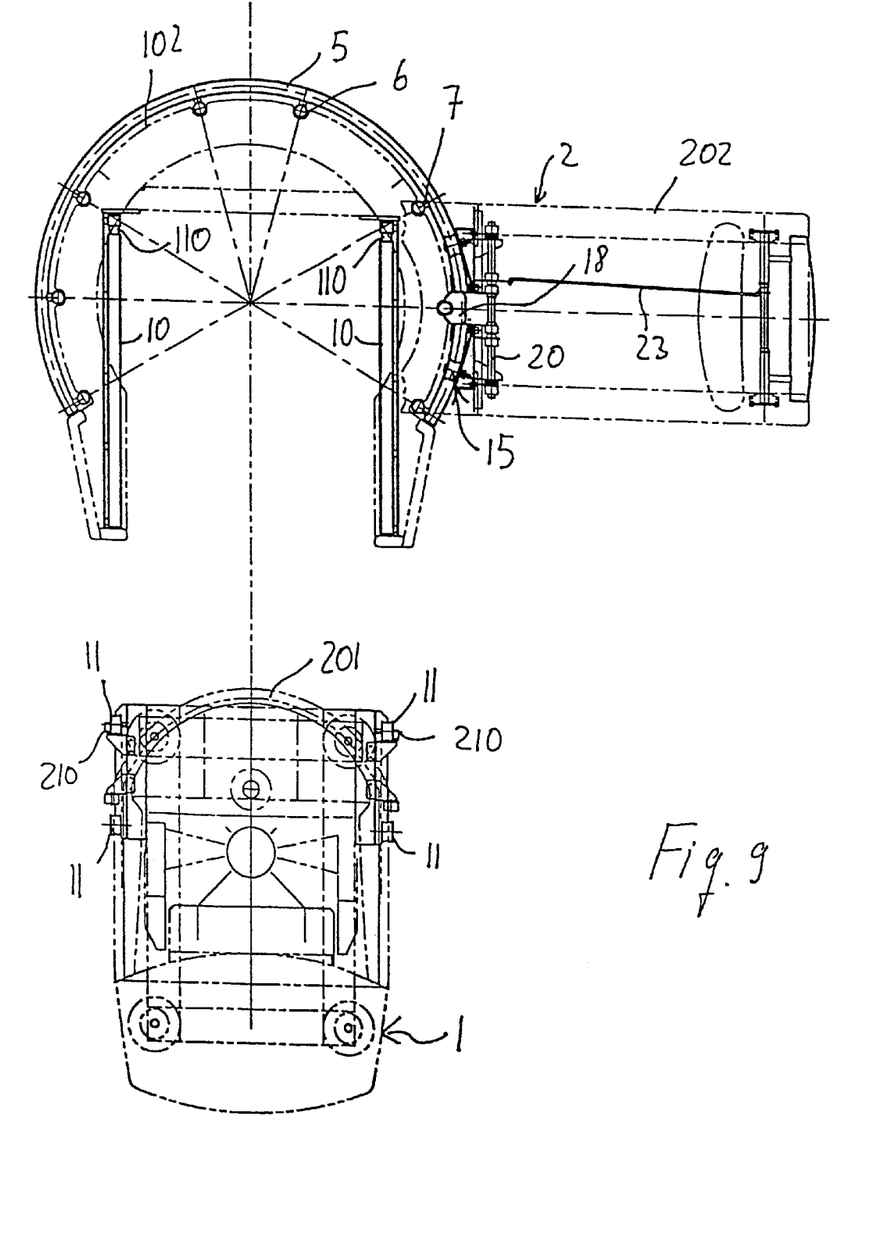
Figure 10:
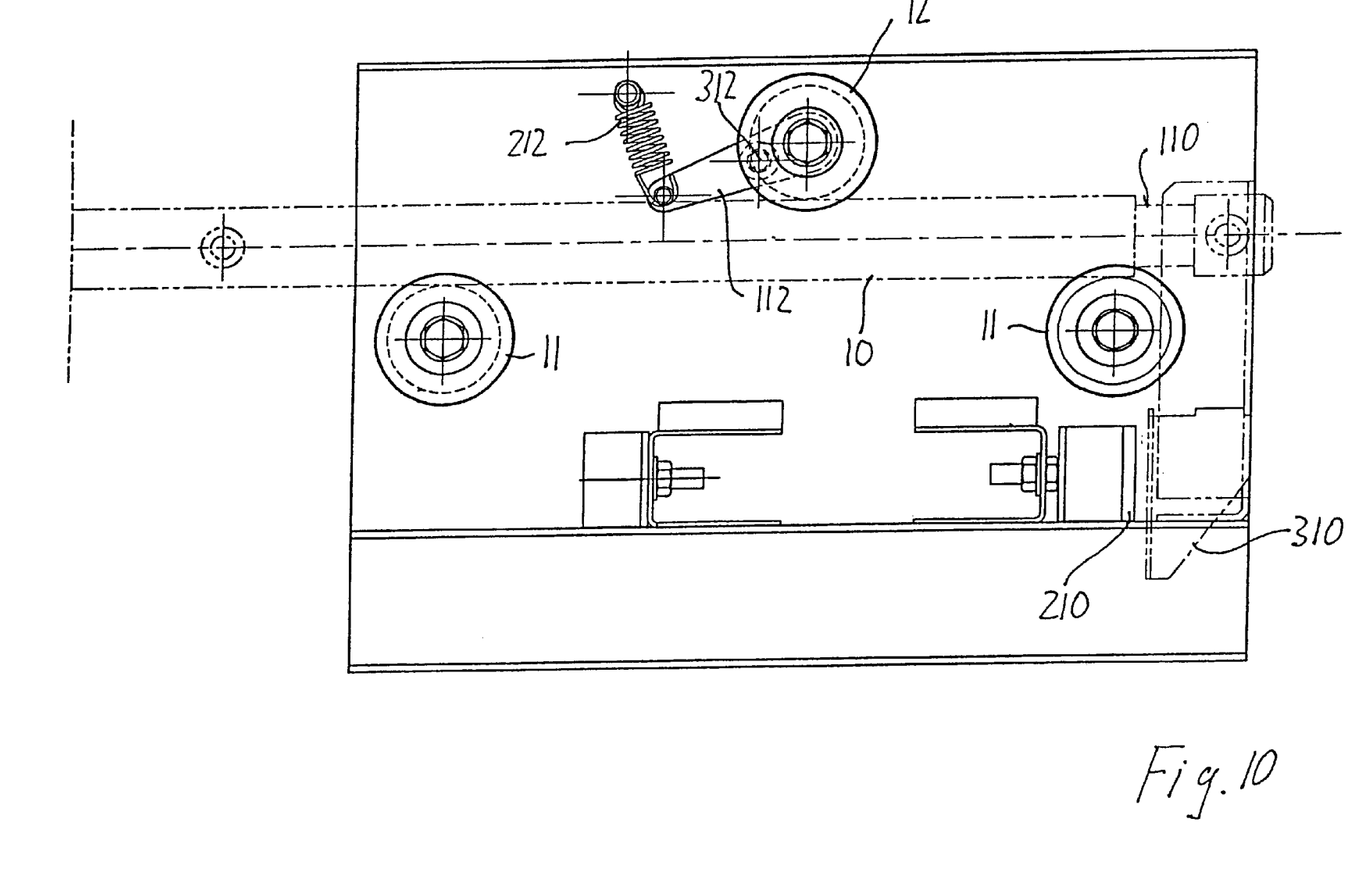
FIG. 10 shows a detail of the sliding means for coupling the table and the magnet as shown in the previous figures.
Figure 11:
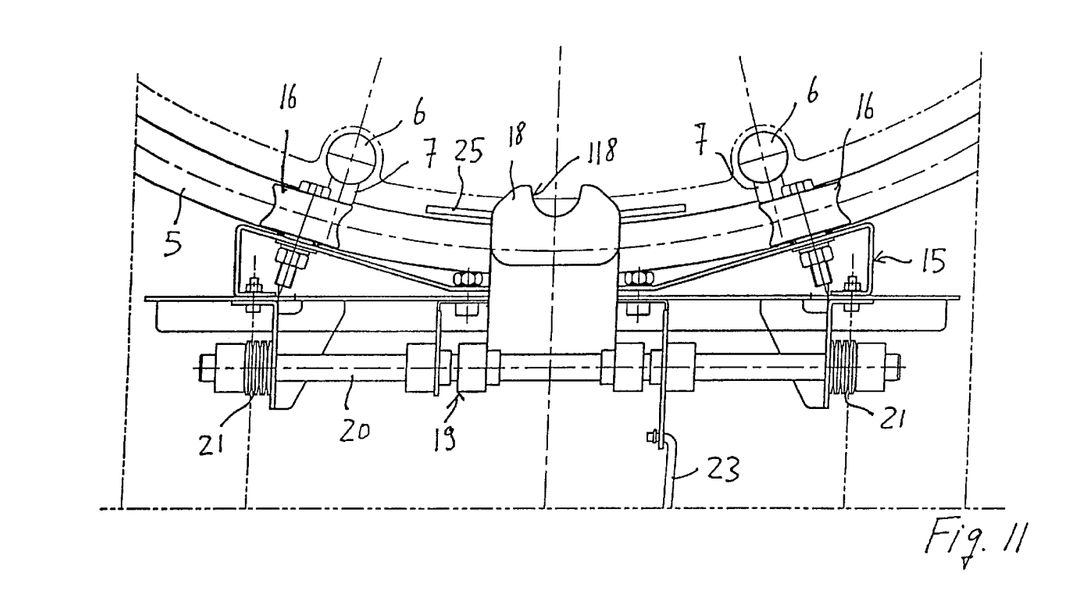
FIG. 11 is a top plan view of a detail of the means for locking the two parts of the table in the different mutual orientation positions.
Figure 12:
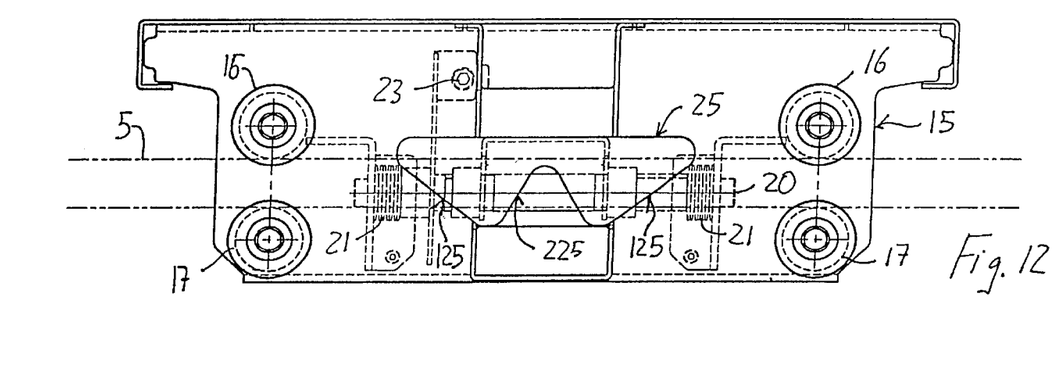
FIG. 12 is a front view of the detail as shown in FIG. 11.
Figure 13:
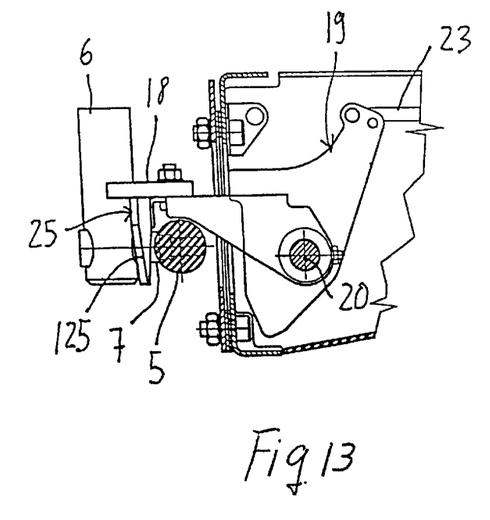
FIGS. 13 and 14 are lateral views of the details as shown in FIGS. 11 and 12 with the locking members being in the engaged and released positions.

This arrangement may be obtained in any way. In the illustrated embodiment the machine 1a carries, a sliding guide consisting of vertically opposite rolls 11, 12 spaced according to the thickness of 2 guide bar 10, carried by each branch of the U-shaped hollow 302 of the part 102 of the table.

Particularly, the guide bar is engaged between a pair of lower rolls 11 and an upper roll 12. All the rolls have an annular peripheral throat having a semicircular or substantially semicircular profile, so that the guide bar can be also held, to a certain extent, in a horizontal transverse direction. The upper roll 12 is preferably supported in such a manner as to yield against a predetermined elastic compressive force directed towards the opposite pair of rolls 11.

This arrangement is obtained by providing an oscillating arm 112, pivoted at its center to oscillate about an axis parallel to that of the roll 12, whereas said roll is mounted on an end of the arm, the other end being connected to a spring, which is fastened to the bearing structure of the machine.

Moreover, the guide bar may have radial recesses, such as annular throats 111 or radial annular projections, which, in combination with the elastically supported roll 12, define predetermined positions, easily changeable by acting with a certain force in the push or pull direction. In combination therewith, the guide bars 10 and/or parts of the machine 1a and/or parts of the part 102 of the table may have spring and/or shock-absorbing end-of-stroke abutments.

As is apparent from FIGS. 6 to 9 and 11 to 14, the part 202 is engaged on the arched guide 5 by a cart 15 (see FIG. 12), disposed at the end side of the part 202, which faces the part 102. The cart 15 has a pair of upper wheels 16 and a pair of lower wheels 17, which are supported with their axes being oriented radially with respect to the arched guide and which, like the rolls 11 and 12 have peripheral throats, whose transverse profile is substantially semicircular or the like. The arched guide 5 also preferably has, without limitation, a circular section. The arched 5 guide is supported in such a manner as to project downwards and radially out of the supporting plane of the part 102 of the table by vertical pins 6, arranged along the extension of the guide 5, whose lower ends are connected to the arched guide by radial fingers 7. The vertical pins 6 may be arranged in any order along the arched guide 5, for instance equally spaced or in such an arrangement as to provide reference points for predetermined orientations of the so-called outer part 202 of the table to the part 102, which is coupled to the side 201 of the magnet 1. In an intermediate position between the wheels 16 and 17, a member 18 for hooking the vertical pins 6, i.e. the pins which lock the part 202 of the table in a predetermined angular position, is provided. The hook-like member 18 consists of a plate having a central U-shaped hollow 118, which is designed to engage the locking vertical pins 6 therein. The hook-like plate is carried by a lever or fork 19, which is supported in such a manner as to be able to oscillate about a horizontal axis 20 transverse to the longitudinal axis of the part 202 of the table. Two elastic members 21, e.g. two helical springs inserted on the corresponding ends of the axis 20 and connected by one of their ends to said axis 20 and by the other end to a stationary abutment of the structure of the table 202, stably stress the lever or fork 19 in such a manner that the latter draws the hook-like plate 18 into a horizontal position, in which it extends into radial engagement of the vertical locking pins 6. A tie rod 23, connected to the lever or fork 19 is also connected to a lever for manual disengagement 24 at the free end of the part 202 of the table. By operating said lever 24, the supporting lever or fork 19 is moved backwards, causing the hook-like plate 18 to oscillate into radially retracted disengagement of the vertical locking pins 6.

According to an improvement, in order to allow the hook-like plate 18 to be easily automatically hooked to a vertical locking pin, a cam 25 is fastened to the plate. This cam consists of a vertically downwardly projecting plate. The plate-like cam 25 has, along its lower edge, a W profile, in which the outer branches 125 are less inclined than the inner branches 225. The plate-like cam 25 extends vertically downwards so as to cooperate by its profile, with the radial fingers 7, which act as stationary abutments for controlling it. The outer inclined branches 125 form guiding surfaces which, when the cart is moved along the guide, cooperate with one corresponding radial finger 7. As is apparent from FIGS. 13 and 14, the cam 25 causes the hook-like plate to progressively lift into disengagement from the vertical pins, allowing it to pass over the relevant vertical locking pin. When the radial finger 7 passes the lower apex and penetrates between the two inner inclined branches 225 of the plate-like cam 25, the hook-like plate lowers again into engagement of the relevant vertical locking pin 6, which is in the correct position to be engaged in the hollow 118. The W shape of the plate-like cam allows to make use of said automatic snap engagement functions with the locking pins 6 for movements in either direction.

Figure 15:
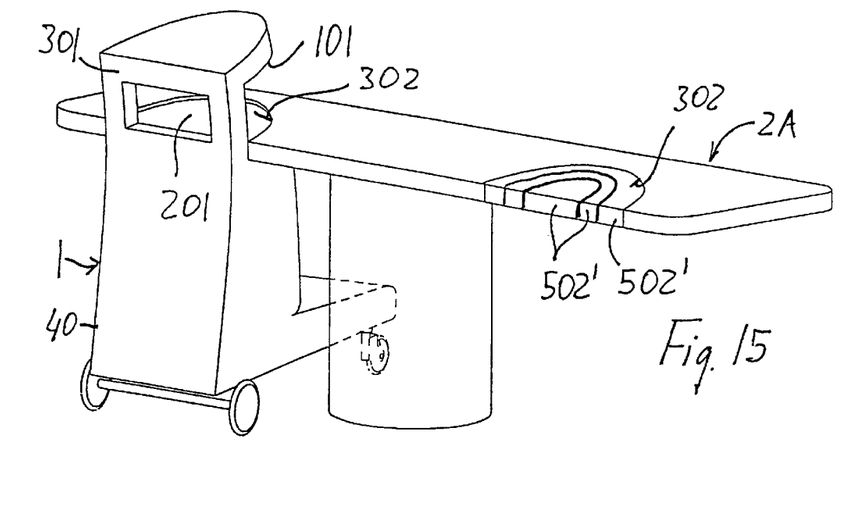
FIGS. 15 and 16 show a second embodiment of the invention.
Figure 16:
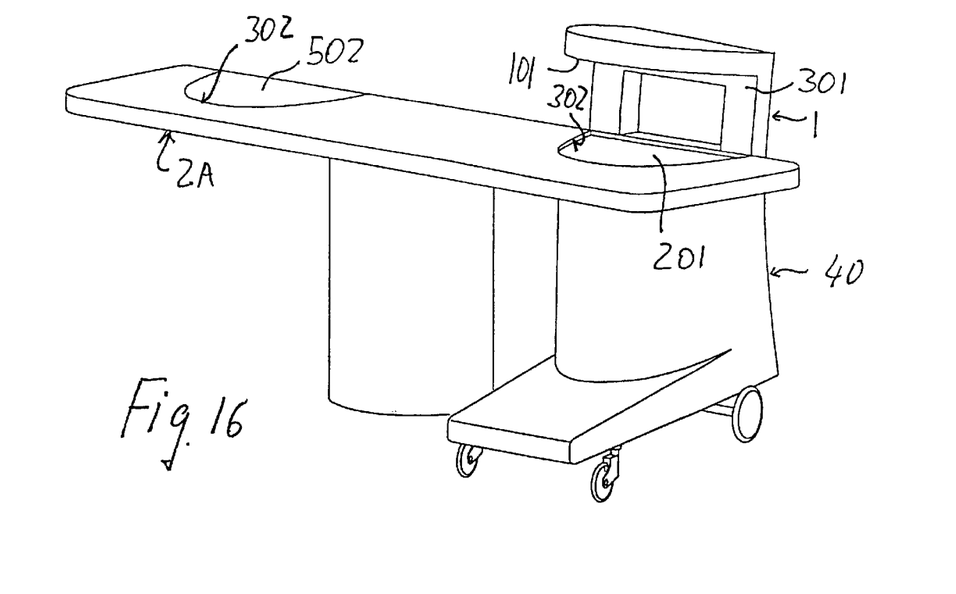

FIGS. 15 and 16 show a second embodiment of the invention. In this exemplary embodiment, the magnet 1 has a comparatively small size as regards the surfaces of the sides 201 and 101, and especially the depth of the lower side 201 of the magnet 1 is smaller than the overall width of a table 2A of an approximately conventional size.

The dimension towards the closed or substantially closed vertical wall 301 is also a submultiple of the length and/or width of the table 2A. In this example, the side 201 has an arched or semicircular or U shape. The table 2A has, in the area substantially corresponding to the shoulder and to the upper limbs and in the area corresponding to the leg and to the lower limbs of a patient, a recess 302, which can be normally closed or filled 10 by a removable, complementarily shaped member 502. This removable complementary member 502 may be, for example, inserted in and removed from its position by using simple sliding guides (not shown in detail), which can consist of a peripheral throat formed in the wall of the recess 302 or of the completion member 502 and of a rib formed in the peripheral wall of the other part.

As shown in the figures, the recesses 302 have such a size that they do not affect the comfortable support of the patient on the table 2A, since they can be bridged by the patient body with no effort and ensuring the support thereof.

When the width of the table allows to do so, a recess 302 may be also provided at one end of the table 2A, for head and neck testing. However, the configuration as shown in the figures also allows head and neck testing by appropriately positioning the patient on the table without affecting his/her support and comfort.

The magnet is small and may be mounted on a cart structure 40. The table, shown in the figures as stationary, may be also provided with supports in the form of a cart.

Figure 14:
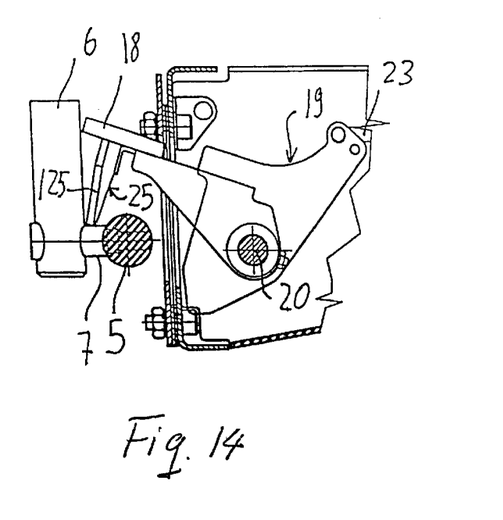

According to FIG. 14, there might be provided a set of inserts 502' which progressively reduce the dimension of the recess 302 in order to adapt these dimensions to different sizes of working surfaces 201.

These inserts 502' can be coupled to each other and to the recess of the table like modular elements, and modules might have different shapes, so as to allow them to fit the different possible shapes of the operating surfaces 201. The coupling elements might be mechanical, such as pins and correspondent insert holes in the facing surface of adjacent inserts modules 502'. Alternatively or in combination the coupling means might be for example straps of the kind of the so called VELCRO™. Further known coupling means that might appear obvious to the expert of the art may be used alternatively or in combination with the above cited ones. This feature is only shown in combination with the table of FIG. 14 but it might as well applied to the table according to the previous embodiment of the invention according FIGS. 1 to 13.

Obviously, the invention is not intended to be limited to the above description and illustrations, but may be greatly varied, especially as regards construction, without departure from the guiding principle disclosed above and claimed below.

What is claimed is:

1. A system for diagnostic or therapeutic treatment of a patient, the system comprising:
   a table for supporting a patient, the table including a patient-supporting surface and a recess extending therethrough and being open at a peripheral edge of the supporting surface, and
   a machine for diagnostic or therapeutic treatment, the machine including a side surface shaped complementary to the recess, wherein the side surface and the recess can be removably merged together so that the patient-supporting surface lies flush with an operating surface of the machine.

2. The system according to claim 1, wherein the patient supporting surface is sized to accommodate at least a part of a patient's body.

3. The system according to claim 1, wherein the table further includes an insert for filling-in the supporting surface, the insert being removable.

4. The system according to claim 3 wherein the insert is slidable into or from the recess.

5. The system according to claim 1, wherein the insert comprises a plurality of modular elements that can be selectively combined in the recess to vary a size of the recess.

6. The system according to claim 1, wherein the recess has a substantially smaller size than the overall supporting surface of the table such that it can be bridged by a portion of a patient's body without affecting the support thereof.

7. The system according to claim 1, wherein the table includes a plurality of recesses spaced apart along the peripheral edge.

8. The system according to claim 1, wherein the table further including a coupling element for attaching the table to the machine.

9. The system according to claim 1, the table comprising first and second parts joined together for rotation relative to one another.

10. The system according to claim 9, wherein the first part of the table is provided, at its periphery facing the second part, with an arcuate guide, the second table part carrying a sliding cart slidably mounted in the arcuate guide.

11. The system according to claim 10, wherein the recess is formed in the first part at a side thereof disposed opposite the second part, the first part comprising a U-shaped frame.

12. The system according to claim 10, wherein the recess has a U shape, and the peripheral edge has a circular shape coaxial with the guide.

13. The system according to claim 9, the table further including a releasable locking mechanism for locking the first and second parts in selected relative angular positions.

14. The system according to claim 13, wherein the locking mechanism includes snap-in member biased to automatically snap into a locked position, and being manually movable out of the locked position.

15. The system according to claim 14, wherein the first table part carries an arc-shaped guide to which the second table part is movably mounted, the locking mechanism being carried by the second table part and being releasably engageable with stop elements carried by the guide.

16. The system according to claim 15, further comprising a stop element, wherein the locking mechanism includes a hook and a cam connected to the hook for engaging abutments and thereby displacing the hook to a position, wherein the hook can be biased into engagement with a stop element when becoming aligned therewith.

17. The system according to claim 16, wherein the hook comprises a W-shaped plate having a hollow which is engageable with the stop element, and there are two of the cams disposed on the plate on opposite sides of the hollow, the hook being biased by a spring to a locking position.

18. The system according to claim 17, wherein the stop elements comprise vertical pins arranged along the guide, and the abutments comprise generally horizontal fingers arranged along the guide, the hook being rotatable about a horizontal axis arranged substantially tangential to the guide.

19. The system according to claim 18, wherein the hook is arranged such that a portion thereof containing the hollow swings upwardly when moving to an unlocking position.

20. The system according to claim 19, wherein the fingers connect the guide to lower ends of the pins, thereby acting as means for supporting the guide.

21. The system according to claim 9, wherein each of the first and second table parts has two support legs disposed so that the table is self-supporting, whereas each of the first and second table parts is non self-supporting.

22. The system according to claim 9, wherein each of the first and second table parts has enough support legs to be self-supporting.

23. The system as claimed in claim 1 wherein the machine comprises a Nuclear Magnetic Resonance Imaging machine having a C-shaped magnet, with a cavity accessible from three sides of its perimeter, and having upper and lower horizontal surfaces delimiting the cavity and covering a magnetic structure of the machine and in which the lower horizontal surface comprises the operating surface.

24. The system as claimed in claim 1 wherein one of the machine and the table carries an elongate projection insertable horizontally into a receptor of the other of the machine and the table when the side surface and the recess are merged together.

25. The system according to claim 24 wherein the receptor comprises vertically spaced rollers rotatable about respective horizontal axes.

26. The system according to claim 25 wherein outer peripheral surfaces of the rollers are recessed.

27. The system according to claim 25 wherein at least one of the rollers is elastically biased toward the projection.

28. The system according to claim 1 wherein the table comprises first and second parts, the first part carrying the recess, and the second part being movable horizontally to selected angular positions relative to the first part.

29. The system according to claim 28 wherein the first table part carries an arcuate guide, and the second table part is movably secured to the guide.

30. The system according to claim 29 wherein the second table part carries rollers which roll along the guide.

* * * * *